United States Patent [19]

Chang

[11] Patent Number: 5,428,133
[45] Date of Patent: Jun. 27, 1995

[54] CHIMERIC ANTI-HUMAN IGE-MONOCLONAL ANTIBODY WHICH BINDS TO SECRETED IGE AND MEMBRANE-BOUND IGE EXPRESSED BY IGE-EXPRESSING B CELLS BUT NOT TO IGE BOUND TO FC RECEPTORS ON BASOPHILS

[75] Inventor: Tse-wen Chang, Houston, Tex.

[73] Assignee: Tanox Biosystems, Inc., Houston, Tex.

[21] Appl. No.: 808,034

[22] Filed: Dec. 11, 1991

Related U.S. Application Data

[63] Continuation of Ser. No. 291,068, Dec. 28, 1988, abandoned, which is a continuation-in-part of Ser. No. 226,421, Jul. 29, 1988, which is a continuation-in-part of Ser. No. 140,036, Dec. 31, 1987, abandoned.

[51] Int. Cl.$^6$ .......... C07K 16/18; C12N 5/10; C12N 5/20
[52] U.S. Cl. .......... 530/387.3; 530/388.25; 435/240.27; 435/172.2; 435/70.21; 435/240.2
[58] Field of Search .......... 530/387.3, 388.25; 435/240.2, 240.27, 172.2, 70.21

[56] References Cited

U.S. PATENT DOCUMENTS 4,714,759 12/1987 Whitaker.
4,940,782 7/1990 Rup et al. .......... 530/388.25
5,180,805 1/1993 Gould et al.

FOREIGN PATENT DOCUMENTS 8601533 3/1986 WIPO.

OTHER PUBLICATIONS

Morrison, Science 229:1202–1207, 1985.
Hochman et al., Biochemistry 12:1130–1135, 1973.
Qi et al. Biotechniques vol. 4:214 1986.
Baniyash, M. "Immunochemical Characterization of the Interaction Between Immunoglobulin E and its Receptor" PhD Thesis, Weizmann Int. of Science, Catalogued Aug. 12, 1990 pp. 84–85.
Hook et al. Mol. Immunol. 28:631–639, 1991.
Hook, W. A. et al. "Monoclonal Antibodies Defining Epitopes on IgE" FED Proc. 46:1346 (1987).
Hook, W. A. et al. "Histamine Release by Structural Analysis of LNRH" FED Proc. 44:1523 (1985).
Hook, W. A. et al. "Differential Binding of MABS to Fluid Phase vs. Basophil–Bound IgE" Clinical Research 33:515A (Apr. 1985).
Hook, W. A. et al. "Detection of Different Antigenic Sites on Human IgE Using Monoclonal Antibodies" Fed. Proc. 42:713 (1983).
Hook, W. A. et al. "Monoclonal Antibodies to Human IgE" Fed. Proc. 40:965 (1981).
Hook, W. A. et al. "Heterogeneity of Monoclonal Antibodies which Bind Unheated or Heated Human IgE" Fed. Proc. 41:825 (1982).
Banigish, M. "Relationships Between Epitopes on IgE Recognized by Defined mABS and by the Fc Receptor on Basophils" J. Immunol. 136:588–592 (1986).
Bangish, M. et al. "Inhibition of IgE binding to mast cells and basophils by monoclonal antibodies to murine RE" Eur. J. Immmol., 14:799–807 (1984).

*Primary Examiner*—Paula Hutzell
*Attorney, Agent, or Firm*—Eric P. Mirabel; Giulio A. DeConti

[57] ABSTRACT

Chimeric antibodies which bind to unique antigenic epitopes of IgE (designated ige.b1) which are present on IgE-bearing B lymphocytes but not basophils are described.

2 Claims, No Drawings

CHIMERIC ANTI-HUMAN IGE-MONOCLONAL ANTIBODY WHICH BINDS TO SECRETED IGE AND MEMBRANE-BOUND IGE EXPRESSED BY IGE-EXPRESSING B CELLS BUT NOT TO IGE BOUND TO FC RECEPTORS ON BASOPHILS

RELATED APPLICATIONS

This is a continuation of application Ser. No. 07/291,068 filed on Dec. 28, 1988 (now abandoned), which is a continuation-in-part of U.S. application Ser. No. 226,421, filed Jul. 29, 1988 (pending), which is a continuation-in-part of U.S. application Ser. No. 140,036, filed Dec. 31, 1987 (abandoned).

BACKGROUND

The immediate-type hypersensitivity, such as extrinsic asthma, hay fever, and allergic responses to certain food or drugs, is mediated primarily by immunoglobulin E (IgE). In an IgE-mediated allergic response, the allergen binds to IgE on the surface of mast cells and basophilic leukocytes (basophils). This binding causes a crosslinking of the IgE molecules and hence the underlying receptors for the Fc portion of IgE (FcεR) and thereby triggers the release of pharmacologic mediators such as histamine, slow-reacting substance of anaphylaxis and serotonin. The release of these mast cell and basophil products causes the various pathological manifestations of allergy.

Patients affected with IgE-mediated hypersensitivities reactions are often treated with histamine antagonists to alleviate symptoms. In addition, during hay fever seasons, desensitization procedures are used to prevent or to alleviate persistent, lasting allergic reactions. In these procedures, small doses of allergen are injected periodically to induce certain, not-fully-understood immune responses that somehow reduce the IgE-mediated responses. Densensitization procedures have been effective in certain patients and only marginally effective in others.

It has been suggested that IgE-mediated allergy might be treated by inhibiting the binding of IgE to mast cells and basophils. For example, synthetic peptides representing various regions of the Fc of IgE (Fcε) have been explored as competitive inhibitors for the binding of IgE to the receptors on mast cells and basophils. See e.g., Stanworth, D. R., *Molec. Immun.* 21:1183–1190 (1984); Stanworth, D. R. and Burt, D. S., *Molec. Immun.* 23:1231–1235 (1986); Burr, D. S. et al., *Molec. Immun.* 24:379–389 (1987); Hahn, U.S. Pat. No. 4,683,292; Hamburger, U.S. Pat. Nos. 4,171,299 and 4,161,522. However, presumably due to the much lower affinity of these peptides compared with whole IgE for the FcεR, such peptides have not been proven highly efficacious for treatment of allergy.

In recent years, monoclonal antibody methodologies have been employed to map the various antigen and functional epitopes on IgE. Baniyash and Eshhar (*Eur. J. Immunol.* 14:799–807 (1984)) reported that among the several rat monoclonal antibodies made against IgE, three inhibited the binding of mouse IgE to rat basophils cells. Since the antibodies could also induce serotonin release from basophils bound with IgE, the antibodies probably bound sites on Fc, which were near but not in the site binding to the receptors for IgE on basophils. More recently the same investigators developed a monoclonal antibody that could inhibit the binding of the IgE to basophilic cells but does not recognize IgE on basophil surface. Baniyash et al., *Molec. Immunol.* 25:705 (1988). Siraganian and colleagues (see *Fed. Proc.* 40:965 (1981), *Fed. Proc.* 46:1346 (1987)) reported that among approximately ten mouse monoclonal antibodies made against human IgE, a few could not bind IgE on basophils. They also described that some of these latter monoclonal antibodies could inhibit the binding of human IgE to basophils. These studies have addressed the use of monoclonal antibodies to define the various epitopes or functionally-related peptidic segments on IgE.

Recently, Whitaker described an immunotoxin specific for the IgE isotype and its use in the treatment of allergy. U.S. Pat. No. 4,714,759. The immunotoxin comprises an anti-IgE antibody coupled to a toxin. The intended pharmacologic mechanism of the treatment is that the immunotoxin specific for IgE isotype would kill IgE-producing B cells.

SUMMARY OF THE INVENTION

This invention pertains to the unique antigenic determinants on IgE molecules and to reagents and methods of treating IgE-mediated allergy based on the discovery of these determinants. The antigenic determinants are present on IgE-bearing B-lymphocytes (B cells) but not on basophils and mast cells.

Although IgE is produced by only IgE-bearing B cells, it is present not only on these cells but also on mast cells and basophils. IgE has a very high affinity for the FcεR on the surface of basophils and mast cells (the association constant, Ka, is in the range of $10^9$–$10^{10}$ liter mole$^{-1}$) and the rate of dissociation is very slow (the half life of "on time" is about 20 hours). Thus, IgE is virtually a surface antigen of basophils and mast cells.

The antigenic epitopes on IgE of this invention are present on IgE-bearing B cells but not on basophils or mast cells and, because of this, the epitopes are unique surface markers of IgE-bearing B cells. The epitopes can be designated ige.b1 (b1 depicts B lymphocytes). The IgE on B cells is the membrane-bound form that is anchored on the membrane by spanning through the membrane lipid bilayer; the IgE on basophils and mast cells is the secretory form that is anchored on the cell surface by binding to the FcεR molecules. The overall structures of the two forms of IgE are somewhat different with the membrane-bound form having an extra segment. The topography of association with the cell surface is also different between the IgE on B cells and on basophils. One class of ige.b1 epitopes are located in the Fc region of the IgE molecule at or near the binding site of FcεR. These epitopes are obscured by FcεR binding. Another class of ige.b1 epitopes are antigenic epitopes located on extracellular segment of membrane-bound region of immunoglobulin heavy chains. In general, these can be designated mb/ec. The mb/ec segment of IgE can be designated ε.mb/ec segment. Reagents which specifically bind to these epitopes and their use in therapy of allergy are described in U.S. patent applications Ser. No. 229,178, filed on Aug. 5, 1988 (abandoned), and Ser. No. 272,243, filed Nov. 16, 1988 (now U.S. Pat. No. 5,091,313), the teachings of which are incorporated by reference herein.

The identification of the ige.b1 epitopes provides for various forms therapy and diagnosis of IgE-mediated allergy based upon agents which specifically bind to the epitopes. These include allergic diseases such as extrinsic bronchial asthma, allergic rhinitis or hay fever, and food and drug allergies. The preferred agents which specifically bind to the epitopes are monoclonal antibodies or fragments thereof. However, for purposes of the therapeutic methods of this invention, the specific binding agent can be any molecule which specifically binds to the epitopes (and thus binds IgE-bearing B cells but not basophils). These reagents include synthetic peptides which are indentical or analogous to the antigen binding region (variable of hypervariable regions) of anti-ige.b1 antibodies. Although the description below focuses mainly on anti-ige.b1 antibodies, the concept and methodologies are equally applicable to other molecules specific for the unique epitopes described herein.

Monoclonal antibodies specific for an ige.b1 epitope can be used to selectively destroy IgE-producing cells. Because the epitope is present on IgE-bearing B cells and not on mast cells or basophils, monoclonal antibodies specific for an ige.b1 epitope bind B cells, but not mast cells or basophils. This differential binding allows the targeting and selective elimination of IgE-producing B cells. The antibodies, either free or in toxin-conjugated form, can be used to target and eliminate the B cells. The monoclonal antibodies which are specific for the ige.b1 epitope at or near the FcεR site of binding to IgE may have additional therapeutical effects. The antibodies bind IgE forming immune complexes, facilitating the removal of IgE from the immune system by the reticuloendothelial system.

This invention also pertains to parotope-specific, anti-idiotypic antibodies of the antibodies reactive with ige.b1 epitopes, to peptides which are modeled after the epitopes (e.g., the site of FcεR binding) and to the use of the anti-idiotypic antibodies and the peptides to treat IgE-mediated allergic diseases.

DETAILED DESCRIPTION OF THE INVENTION

1. Unique Epitopes of Immunoglobulin E

This invention is based on the discovery of uniquely situated epitopes of IgE (ige.b1). The epitopes are present on IgE-bearing B lymphocytes but not on mast cells and basophils. One class of ige.b1 epitopes is located at or near the binding site for FcεR. The presence of these epitopes only on IgE-bearing B cells follows from the fact that the epitope is obscured when IgE is bound to FcεR on basophils and mast cells. The ige.b1 epitopes may possibly be composed of several antigenically discrete sites and each of them can be defined by its reactivity with a monoclonal antibody which reacts with IgE-bearing B cells, but not basophils, such as E8-5-3, E11-4-70, E101-1, and E10-12-55 (see below). The cell line producing E11-4-70 was deposited at the American Type Culture Collection, Rockville, Md., on Nov. 8, 1990, under Accession No. and will be available for inspection once this application issues as a patent. Because IgE is present on the surface of only three cell types in the body, IgE-bearing B cells, basophils, and mast cells, these ige.b1 epitopes are virtually unique cell surface marker of IgE-bearing B cells. These new markers provide for several types of therapy of IgE-mediated allergic diseases.

2. Monoclonal Antibodies Which Bind IgE-Bearing B Cells But Not Basophils

Monoclonal antibodies specific for the ige.b1 epitopes bind IgE on the surface of IgE-producing B cells but do not bind basophils. This differential binding of IgE-bearing cell types provides a basis for therapeutic and diagnostic uses for the antibodies.

It is crucial that the antibodies do not bind basophils and induce histamine release. One of the most powerful agents that trigger the release of pharmacological mediators of allergy from mast cells and basophils is anti-IgE antibody. Conventional anti-IgE antibody will bind IgE on the surface of mast cells and basophils and trigger the release of pharmacological mediators or allergy. The antibodies of this invention cannot bind IgE on these cells because the cognate epitope is masked and thus they do not induce the release of histamine from these cells.

3. Therapy of IgE-mediated Allergy Based Upon the Selective Elimination of IgE-producing Cells

A. Antibodies Specific for IgE-producing Cells

The antibodies specific for IgE-producing B cells, as murine, human, or mouse/human chimeric antibody, may be applied in several ways for the treatment of IgE-mediated allergies. For this purpose, the antibodies can be used to selectively deplete IgE-bearing B cells. The antibodies can be used as an effector agents mediating an immune function or as a carrier agent of toxins or cytotoxic drugs, as set forth below, for delivering an effector substance.

Among the various immune functions that an antibody specific for a surface antigen on target cells can mediate are antibody and complement-mediated cytolysis and antibody-dependent cellular cytotoxicity (ADCC). The antibody may also mediate immune regulatory functions. Antibodies of certain IgG subclasses, such as mouse IgG2a and human IgG1 and IgG3, can mediate (ADCC) carried out by certain Fc receptor-bearing phagocytic leukocytes. For example, OKT3, a mouse IgG2a monoclonal antibody specific for human T cell surface antigen (the first monoclonal antibody approved by FDA for marketing as a therapeutical agent) is used in patients to provide rapid depletion of T cells in the blood and to induce an immunosuppressed state (for kidney transplantation). Russell, P. S. et al., Annu. Rev. Med. 35:63–79 (1984); Norman, D. J. et al., Transpl. Proc. 17:39–41 (1985). OKT3, at a dosage of 5 mg/day/subject, can deplete completely circulating T cells. The antibodies of this invention, especially in the form of mouse gamma 2a antibodies or chimeric antibodies bearing human gamma-1 or gamma-3 chains, can be used to deplete IgE-bearing B cells by the ADCC mechanism. The antibodies can be administered as free antibodies to patients afflicted with IgE-mediated allergy in amounts sufficient to eliminate substantially IgE-producing cells and consequently, to deplete substantially IgE. For example, the amount can range from 1–50 mg/dose/subject. The treatment may involve one or several injections. The duration of the presence of antibody and the amount of antibody needed to eliminate B cells is less than that necessary to continuously inhibit the binding of IgE to basophils and mast cells.

For therapeutic uses described, human antibodies are most preferred. Human antibodies, however, are difficult to produce in large quantity. As an alternative, chimeric or "near-human" antibodies are preferred. Chimeric antibodies comprise a variable or antigen binding (hypervariable or complementarity determining) region derived from an animal (e.g., a mouse) antibody and the remaining regions derived from a human antibody. Methods for producing chimeric (e.g. murine/human) antibodies are described below. Chimeric antibodies can be produced in large quantities and they are less immunogenic in humans than nonhuman antibodies. Consequently, they are better suited for in vivo administration than animal antibodies, especially when repeated or long term administration is necessary. Antibody fragments of the chimeric antibodies can also be used.

Immunotherapies employing the antibodies of this invention may be used in combination with conventional desensitization immunotherapy. For example, desensitization with allergen may be performed in conjunction with the administration of anti-ige.b1 antibodies or immunotoxins (see B section below) to eliminate substantially IgE-producing cells. One major effect of desensitization is that IgG's are induced against the allergen/immunogen. The induction of an IgG response may be most effective when IgE-producing B cells are substantially depleted. The combination of antibody and desensitization therapy is an attractive form of therapy. IgE-producing B cells may be temporarily depleted (for a few weeks or months) by the anti-ige.b1 antibody and will eventually repopulate. The desensitization may have longer lasting effects.

B. Immunotherapy Combining an ige.b1-specific Antibody and a Factor Enhancing ADCC Many factors, such as GM-CSF (granulocyte monocyte-colony stimulation factor) or M-CSF (monocyte-colony stimulation factor), are known to induce the proliferation of leukocytes, including those mediating ADCC. In in vitro experiments, GM-CSF and M-CSF have been shown to augment the ADCC activity on tumor cells mediated by monoclonal antibodies specific for surface antigens expressed on the tumor cells. It is conceivable that the therapeutical effect of ige.b1 specific monoclonal antibodies in treating allergies can be enhanced by combining the use of factors that augment ADCC activities.

C. Immunotoxins Specific for IgE-producing Cells

The ige.b1 epitopes provide highly specific targets for immunotoxins directed against IgE-producing B cells. Immunotoxins specific for the epitopes bind to IgE-producing B cells but not to mast cells or basophils. In this way, IgE-producing B cells can be selectively reduced or eliminated in a patient suffering from an IgE-mediated allergy. The reduction of the IgE producing cells reduces IgE levels in the circulation which results in a reduction of the amount of IgE available to bind mast cells and basophils. The immunotoxin does not kill mast cells or basophils and cause the release of pharmacologic mediators from these cells.

Immunotoxins for selective binding to IgE-producing lymphocytes are comprised of cytolytic or cytotoxic agents conjugated to a binding agent specific for an ige.b1 epitope. The preferred specific binding agents are anti-ige.b1 antibodies or fragments thereof (e.g., F(ab)'$_2$ Fab F$_v$ or analogues or derivatives thereof). The cytolytic agents can be selected from any of the available substances including ricin, Pseudomonas toxin, diphtheria toxin, pokeweed antiviral peptide, trichothecenes, radioactive nuclides, and membrane-lyric enzymes. The antibody and the cytotoxin can be conjugated by chemical or by genetic engineering techniques.

The immunotoxins are administered to a patient afflicted with IgE-mediated allergy in amounts sufficient to reduce or to eliminate IgE-producing lymphocytes in the patient and thereby prevent or alleviate the symptoms of the IgE-mediated allergy. The immunotoxins may be used alone or in combination with free anti-IgE antibody.

4. Removal of IgE by Monoclonal Antibodies Which Do Not Bind IgE on Basophils and Mast Cells In certain embodiments, the monoclonal anti-IgE antibodies of this invention bind to an ige.b1 epitope located at or near the Fc$\epsilon$R binding site on IgE. In so doing, the antibodies block the binding site on IgE for mast cells and basophils and this contributes partly to their therapeutical efficacy. In order to achieve this possibly beneficial additional therapeutical mechanism, the antibodies must bind specifically to the epitope with an affinity which is greater than the affinity with which the Fc$\epsilon$R binds IgE. This combination of specificity and affinity provides for effective inhibition of IgE binding to Fc$\epsilon$R at pharmaceutically feasible concentration. In addition, the immune complexes of IgE and the monoclonal antibodies may be removed rapidly by cells of the reticulo-endothelial system. Upon the intravenous injection of the monoclonal antibodies, most IgE molecules in the circulation probably form immune complexes and are removed rapidly. These mechanisms will reduce the levels of free IgE in the body of the treated patient, whenever the therapeutic monoclonal antibodies are present in sufficient levels. These various mechanisms should contribute to the short term effects of the therapeutic antibodies. However, long-term therapeutic effects probably can be achieved without these mechanisms.

Affinity can be represented by the affinity or association constant, Ka. The Fc$\epsilon$R of mast cells and basophils has an estimated Ka in the range of $1 \times 10^9 - 1 \times 10^{10}$ liter/mole. See Kulczycki, A., *New Trends in Allergy II* ed. by Ring, J. and Burg, G., pp. 25–32, Spring-Verlag, New York, 1986. Thus, a monoclonal anti-IgE antibody will effectively compete with Fc$\epsilon$R, if its affinity constant for IgE is about or greater than $1 \times 10^9$ liter/mole. In general, monoclonal antibodies have, Ka's, below $1 \times 10^9$ liter/mole. Consequently, although an antibody might be appropriately specific for the epitope(s) described and suitable for eliminating IgE-bearing B cells by mechanisms described above, it may not have this additional therapeutic effect, if it does not have a Ka sufficient to compete effectively with Fc$\epsilon$R for IgE at pharmacologically feasible concentrations.

In preferred embodiments, the monoclonal anti-IgE antibodies of this invention have a Ka for IgE which is comparable or greater than the affinity of Fc$\epsilon$R for IgE. Mast cells and basophils in the body are bound with IgE; in most individuals a large proportion of the Fc$\epsilon$R are saturated by IgE. The IgE molecules have a very long half lives of "on" (receptor occupancy) time of about 20 hours. Kulczycki, A., *J. Exp. Med.* 140:1976 (1974). When the IgE molecules dissociates from the mast cells or basophils, the high affinity anti-ige.b1 antibodies administered to the patient will tightly bind them and inhibit their reassociation with Fc$\epsilon$R. Because IgE molecules have long "on" time and dissociate slowly from the basophils and mast cells, the therapeutic effects probably will be attained only a few days after the treatment (or even longer) when a significant portion of the IgE on basophils and mast cells have dissociated from Fc$\epsilon$R and have been complexed or cleared away by the anti-IgE antibody. When this is achieved, the density of IgE molecules bound to Fc$\epsilon$R molecules on basophils and mast cells is substantially decreased and consequently, allergens are unable to cross-link sufficient numbers of Fc$\epsilon$R to induce histamine.

5. Diagnostic Uses of Antibodies Which Specifically Bind IgE-producing Cells The antibodies against ige.b1 eptiopes can be used to identify and enumerate IgE-bearing lymphocytes in mixed leukocyte populations. For this purpose, The antibodies can be used in standard assay formats for determining cell surface antigens. In general, the antibody is contacted with a sample of the leukocytes to be tested under conditions which allow the antibody to bind IgE-bearing cells in the sample. The cells are then examined for binding of antibody. This can be accomplished by conventional cell staining procedures. For example, a fluorescently labeled second antibody can be used to detect binding of the anti-IgE antibody.

6. Antiidiotypic Antibodies and Methods of Active Immunization Against IgE

The ige.b1-specific monoclonal antibodies described thus far can be used to generate parotope-specific, anti-idiotypic antibodies which offer another mode of treating IgE-mediated allergy. Antibodies against the parotope of the ige.b1-specific antibodies conformationally resemble the epitope for which the anti-IgE antibody is specific, that is, they resemble an ige.b1 epitope. These anti-idiotypic antibodies can be used to actively immunize against ige.b1 and induce the endogenous formation of antibodies against the ige.b1 epitope. The induced antibodies will mediate the various therapeutical effects of ige.b1-specific antibodies.

Because IgE is a "self-molecule", it is generally not immunogenic. However, active immunization against IgE may be achieved by using the parotope-specific antibodies of this invention. The parotope-specific antibody shares conformational resemblance with the antigen—the ige.b1 epitope—which can elicit immune response in humans against the epitope.

Paratope-specific, anti-idiotyptic antibodies are administered to a patient suffering from IgE-mediated allergy in an immunogenic amount to induce the formation of ige.b1 antibodies. The anti-idiotypic antibodies are preferably administered as chimeric antibodies. They may also be given as antibody fragments (which also may be chimeric in nature) or analogues.

7. Production of the Monoclonal Antibodies of this Invention

The monoclonal anti-IgE and anti-idiotypic antibodies of this invention are produced by continuous (immortalized), stable, antibody-producing cell lines. The preferred antibody-producing cell lines are hybridoma cell lines and myeloma cell lines. In principle, however, the cell lines can be any cells which contain and are capable of expressing functionally rearranged genes which encode the antibody variable regions of the antibody light and heavy chains. Preferably, the cell line should have the capability to assemble the chains into functional antibodies or antibody fragments. Thus, lymphoid cells which naturally produce immunoglobulin are most often employed. In addition to those previously mentioned, examples of suitable lymphoid cells are viral or oncogenically transformed lymphoid cells.

Hybridoma cells which produce the anti-IgE antibodies of this invention can be made by the standard somatic cell hybridization technique of Kohler and Milstein, *Nature* 256:495 (1975) or similar procedures employing different fusing agents. Briefly, the procedure is as follows: the monoclonal anti-IgE antibodies are produced by immunizing an animal with human IgE, or peptidic segments of human IgE (secretory or membrane-bound), which are identified as potential components of ige.b1 epitope. The peptides can be synthesized and conjugated to a carrier protein, such as keyhold limpet hemocyanin, to be used as an immunogen. Lymphold cells (e.g. splenic lymphocytes) are then obtained from the immunized animal and fused with immortalizing cells (e.g. myeloma or heteromyeloma) to produce hybrid cells. The hybrid cells are screened to identify those which produce the desired anti-IgE antibody.

Human hybridomas which secrete human antibody can be produced by the Kohler and Milstein technique. Although human antibodies are especially preferred for treatment of humans, in general, the generation of stable human-human hybridomas for long-term production of human monoclonal antibody can be difficult. Hybridoma production in rodents, especially mouse, is a very well established procedure. Stable murine hybridomas provide an unlimited source of antibody of select characteristics. Murine antibodies, however, may have limited use in the treatment of humans because they are highly immunogenic and can themselves induce untoward allergic reactions in the recipient. In the preferred embodiment of this invention, the anti-IgE and anti-idiotypic antibodies are produced in a rodent system and are converted into chimeric rodent/human antibodies by the established techniques described in detail below. As explained above, these "near human", chimeric antibodies are preferred for in vivo administration, especially where multiple doses are required.

For the production of the anti-IgE antibodies of this invention, human IgE for immunization can be purified from human serum. Alternatively, human IgE may be produced by culturing an IgE-producing cell line (for example, the cell line U266, ATCC number CRL8033). Human IgE can be purified by affinity chromatography. Mouse monoclonal antibodies specific for human IgE are conjugated to a suitable matrix (such as cyanogen bromide-activated Sepharose 4B) to provide an IgE-specific immunoadsorbent. The IgE preparation can be contacted with the immunoadsorbent which selectively adsorbs IgE. The adsorbed IgE can thereafter be eluted in substantially pure form from the immunoadsorbent.

In preferred embodiments, animals are immunized with a vigorous immunization protocol in order to produce a high frequency of lymphocytes producing IgE-specific antibodies. Spleen cells are obtained from the immunized animal and fused with an immortalizing cells, preferably myeloma cells which have lost the ability to secrete immunoglobulin. Many suitable myeloma cell lines are known in the art. An example is the murine myeloma NS-1. Fusion of the spleen cells and fusion partner can be carried out in the presence of polyethylene glycol according to established methods. Techniques of electrofusion may also be used. The resulting hybrid cells are clonally cultured and then screened for production of anti-IgE antibody.

Hybridomas producing antibodies which are specific for an epitope present on IgE-bearing B cells and absent on basophils and which have an affinity for IgE sufficient to block FceR binding to IgE can be selected as follows. Hybridomas are first screened for production of antibody reactive with human IgE. This can be done by an enzyme-linked immunosorbent assay (ELISA) employing purified human IgE adsorbed to a solid phase.

One way of obtaining generally high affinity antibodies is as follows. The solid phase for the ELISA is coated with very small amounts of human IgE. For example, if a standard microwell plate is used as the solid phase, about 50 ul of a 0.1 ug/ml solution of IgE is used per well. Hybrids are selected which show a comparatively high enzyme activity (optical density level) in the assay. The culture supernatants contain either relatively higher amounts of antibodies or antibodies of relatively higher affinity or both.

Hybridomas are then screened for secretion of antibodies which do not react with basophil-bound IgE. A preferred method is to screen the antibodies for the inability to induce histamine release by basophils. The source of basophils for such histamine release assays is blood leukocytes from donors whose basophils are known to be very sensitive for induction of histamine release. An alternative and possibly less sensitive method is an immunofluorescence staining technique. Basophil leukocytes can be isolated from blood. Freshly isolated basophils have IgE on their surface. Monoclonal antibodies which do not bind basophil-bound IgE are specific for an epitope which is at or near a site occupied by the basophil Fc$\epsilon$R (and hence is inaccessible for the monoclonal antibodies).

Hybridomas which produce parotope-specific anti-idiotypic antibody can be made by immunizing an animal with anti-IgE antibody and screening for antibodies which bind the parotope of the immunizing anti-IgE antibody. Immunization results in production of antibodies against the antigenic determinants on the anti-IgE antibody including the idiotype. Anti-idiotype antibodies are first screened for their binding to anti-IgE antibody and not other mouse antibodies. Those which are parotope-specific are screened on the basis of the antibody's ability to compete the binding of human IgE to the anti-IgE monoclonal antibody used for immunization.

Antibody fragments such as F(ab')$_2$, Fab and F$_v$ can be produced by standard techniques of enzyme digestion. In addition, synthetic peptides representing Fab and F$_v$ analogues can be produced by genetic engineering techniques. See e.g., Better, M. et al. (1988) *Science* 240:1041; Huston, J. S. et al., (1988) *Proc. Natl. Acad. Sci. USA* 85:5879–5883.

The chimeric anti-IgE antibodies are comprised of individual chimeric heavy and light immunoglobulin chains. The chimeric heavy chain is a contiguous polypeptide having a rodent (generally murine) heavy chain variable region or hypervariable regions and a human heavy chain constant region. The chimeric light chain is a contiguous polypeptide having a rodent light chain variable regions or hypervariable regions and human light chain constant region.

The chimeric antibodies can be monovalent, divalent or polyvalent. Monovalent antibodies are dimers (HL) formed of a chimeric heavy chain associated (through disulfide bridges) with a chimeric light chain. Divalent immunoglobulins are tetramers (H$_2$L$_2$) formed of two associated dimers. Polyvalent antibodies can be produced, for example, by employing heavy chain constant region which aggregate (e.g., mu type constant regions).

The variable regions of the chimeric antibodies are derived from the anti-IgE antibody of this invention. The heavy chain constant region can be selected from any of the five isotypes alpha, delta, epsilon, gamma or mu. Heavy chains of various subclasses (such as the IgG subclasses) can be used. The different classes and subclasses of heavy chains are responsible for different effector functions and thus, by choosing the desired heavy chain constant region, chimeric antibodies with desired effector function can be produced. The light chain constant region can be the kappa or lambda chain.

In general, the chimeric antibodies are produced by preparing a DNA construct which encodes each of the light and heavy chains components of the chimeric antibody. The construct comprises fused gene comprising a first DNA segment which encodes at least the functional portion of the murine variable region (e.g. functionally rearranged variable regions with joining segment) linked to a second DNA segment encoding at least a part of a human constant region. Each fused gene is assembled in or inserted into an expression vector. Recipient cells capable of expressing the gene products are then transfected with the genes. The transfected recipient cells are cultured and the expressed antibodies are recovered.

Genes encoding the variable region of rodent light and heavy chains can be obtained from the the hybridoma cells which produce the anti-IgE antibodies. For example, the murine hybridoma cell lines which produce murine anti-IgE antibody provide a source of variable region genes.

Constant regions genes can be obtained from human antibody producing cells by standard cloning techniques. Alternatively, because genes representing the two classes of light chains and the five classes of heavy chains have been cloned, constant regions of human origin are readily available from these clones.

Preferably, the fused genes encoding the light and heavy chimeric chains are assembled into expression vectors which can be used to cotransfect a recipient cell. Suitable vectors for the gene constructs include plasmids of the types pBR322, pEMBL and pUG. Each vector contains two selectable genes—one for selection in a bacterial system and one for selection in a eukaryotic system—each vector having a different pair of genes. These vectors allow production and amplification of the fused genes in bacterial systems and subsequent cotransfection of eukaryotic cells and selection of the cotransfected cells. Examples of selectable gene for the bacterial system are the genes which confer ampicillin and the gene which couples chloramphenicol resistance. Examples of selectable genes for eukaryotes are gpt and neo.

The preferred recipient cell line is a myeloma cell. Myeloma cells can synthesize, assemble and secrete immunoglobulins encoded by transfected antibody genes. Further, they possess the mechanism for glycosylation of the immunoglobulin. A particularly preferred recipient cell is the Ig-nonproducing myeloma cell SP2/0. Shulman et al, *Nature* 276:269 (1978). The cell produces only immunoglobulin encoded by the transfected immunoglobulin genes. Myeloma cells can be grown in culture or in the peritoneum of mice where secreted immunoglobulin can be obtained from ascites fluid. Other lymphoid cells such as B lymphocytes or hybridoma cells can serve as suitable recipient cells.

Lymphoid cells can be transfected with vectors containing immunoglobulin encoding genes in several ways. These include electroporation, protoplast fusion and calcium phosphate precipitation procedure. The resulting transfected cells provide continuous, stable cell lines which produce chimeric antibodies.

The chimeric antibodies can be produced in large quantity in large scale tissue culture systems such as various continuous perfusion systems, hollow fiber systems, static maintenance culture systems or other systems.

Near human antibodies or antibody fragments can also be produced by engineering gene sequences of human antibodies which encode the hypervariable (complementarity determining) regions to provide appropriate anti-IgE specificity. See e.g., Robert, S. et al., *Nature* 328:731-733 (1987); Better, M. et al., (1988) *Science* 240:1041.

8. Peptides Which Block FcεR of Mast Cells and Basophils

This invention also provides peptides which embody the ige.b1 epitopes. The peptides comprise amino acid sequences which are identical or equivalent to the amino acid sequence of an ige.b1 epitope of IgE. For example, the peptides can have sequences corresponding to the epitopes defined by antibodies E8-5-3, E11-4-70, E101-1 and E10-12-55 or other anti-ige.b1 antibodies described below. Peptides which correspond to the binding site of the FcεR can be used to block the binding of IgE to mast cells and basophils.

The invention is further illustrated by the following examples.

EXAMPLE I: PREPARATION OF THE HYBRIDOMAS AND MONOCLONAL ANTIBODIES a) Preparation of Human IgE Human IgE was obtained from a commercial source and purified for immunizing mice to obtain immune splenocytes for fusion and for screening hybrids. The IgE was also used to characterize the various monoclonal anti-IgE antibodies. Two preparations of human IgE were used. One was polyclonal IgE purified from human sera, which was obtained from Ventrex (Portland, Me.). This human IgE was purified from sera by affinity chromatography using Sepharose 4B column conjugated with rabbit IgG specific for human IgE. Contaminating human albumin and transferrin were removed by affinity column conjugated with antibodies specific for albumin and transferrin. Monoclonal human IgE was also produced from culture supernatants of IgE-producing U266 cell line. The IgE was affinity purified on a Sepharose 4B column conjugated with a monoclonal antibody specific for human IgE. This monoclonal antibody IgG was purified from the ascitic fluids of mice bearing the specific hybridomas with a protein A-conjugated column.

The polyclonal and monoclonal human IgE's were analyzed by SDS-polyacrylamide gel electrophoresis under reducing and non-reducing conditions. In both cases, distinctive IgE molecules (under non-reducing conditions) and heavy and light chains (under reducing conditions) were observed and only traces of relatively very light bands of some other contaminating proteins were present. Since the U266 cell line was grown in serum-free, defined medium, we had some clues as to the identity of the contaminating proteins in the monoclonal human IgE preparation.

b. Immunization Procedure
1. Procedure

Male Balb/c mice of initially 6-8 weeks old were used for immunization for preparing immune spleen cells for fusion with myeloma cells to produce hybrids. The polyclonal human IgE purified from sera provided by Ventrex was used as the immunogen. The rationale for this is that the monoclonal IgE produced by U266 cell line might bear certain unknown anomalies. In addition, we did not want to generate monoclonal antibodies against the idiotypes of U266 IgE, and it would be much more likely to induce anti-idiotypic responses against monoclonal antibodies. After performing three fusion experiments with mice immunized with U266-derived IgE, we switched to fusions with mice immunized with polyclonal, human-sera-derived IgE.

For immunization, each mouse was injected with 50 μg of human IgE per injection. The first immunization was given in complete Freund's adjuvant. The mice were injected subcutaneously at sites with high concentrations of lymph nodes, for example, the underside of the intersection of the limbs and the trunk. One month and two months later the mice received subcutaneous booster injections at the same sites with 50 μg IgE. The boosters were prepared essentially in the same manner as was the first injection, except that for the boosters the emulsification was done in incomplete Freund's adjuvant.

After at least another month, each mouse was reimmunized subcutaneously for the last time (the fourth injection) with 50 μg IgE in PBS. Each mouse was injected subcutaneously at the intersection of each limb with the trunk, and intraperitoneally. Three days after the last injection, the mice were sacrificed and their spleens were removed. The spleen cells were then fused with myeloma cells by the following procedure.

c) Fusion

Suspensions containing a five-to-one ratio of spleen cells to myeloma cells were prepared. The myeloma cells chosen were NS-1. The NS-1 cells were conditioned to have a doubling time about every seventeen hours. They were used for fusion when in the log phase. The NS-1 cells were subcultured in bacteriological plates (100 mm) at a concentration of $6 \times 10^4$ cells/ml in 10 ml of Dulbecco's Modified Eagle's Medium (DMEM) containing 5% fetal bovine serum (FBS), 100 units/ml of penicillin and 100 ug/ml of streptomycin. The medium was changed every three days. Alternatively, the cells were subcultured at $1.5 \times 10^5$ cells/ml in 10 ml of the same medium, and the medium was changed every two days.

The spleen cells were prepared by placing the spleen on a bacteriological plate (100 mm) and injecting 20 ml of calcium, magnesium free PBS (CMF-PBS) into both ends of the spleen to loosen up the spleen cells. The spleen cells were then transferred to a 50 ml centrifuge tube.

The spleen cells were centrifuged at 200 g for five minutes, and then suspended in 5 ml of 0.83% $NH_4Cl$ (0.155M) for 10 minutes at room temperature to lyse the erythrocytes. 5 ml of CMF-PBS was added to the tube to stop the lysis. The cells were then pelleted and resuspended in 10 ml of CMF-PBS.

The concentration of lymphocytes was determined by adding 40 μl of cell suspension to 10 ml of saline together with 3 drops of Zap-oglobin TM. The number of lymphocytes was counted with a hemacytometer and the concentration of cells determined.

The NS-1 cells were transferred from bacteriological plates (100 mm) to a 50 ml centrifuge tube. The cell concentration was determined. The NS-1 cells were then suspended in 10 ml of CMF-PBS and mixed with spleen cells at 1:5 in a 50 ml centrifuge tube. Routinely, we obtain $2-5 \times 10^8$ cells from one immune spleen and we use two spleens in each fusion experiment.

The cells were spun down and washed once with 10 ml of CMF-PBS. The supernatant was aspirated as much as possible with a glass Pasteur pipette. The tube was gently tapped to free the cell pellet.

Prior to preparing the cells, a fusion mixture had been prepared as follows. 5 g of polyethylene glycol 1450 (Kodak) had been mixed with 5 ml of CMF-PBS and 0.5 ml of DMSO. This mixture had been warmed to 56° C., titrated to a final pH of 7.0, and filtered through a 0.22μ Millipore filter to sterilize. 1.0 ml aliquots had been added to Cryotubes, and these had been stored at −70° C.

To prepare the fusion mixture for use, one of the aliquots in the Cryotubes was melted by heating it to 37° C. Separately, a tube containing 1.0 ml of DMEM (without serum) was heated to 37° C.

The 1.0 ml aliquot of polyethylene glycol fusion mixture was added to the cell suspension and the suspension was mixed well. Forty-five seconds after the polyethylene glycol fusion mixture had been added, 2.0 ml of the pre-heated DMEM (without serum) was added dropwise with mixing. The remaining 8 ml of the pre-heated DMEM (without serum) was then added. The cells were left at room temperature for 10 minutes.

2.0 ml of FBS was added to the suspension and the suspensions were mixed well. The combination of the FBS and the CMF-PBS can help to prevent adherence of cells to the test tube walls. The suspension were then centrifuged at 400 g for four minutes.

After having been spun down, the cells were suspended in about 120 ml of a modified medium, supplemented with 5% FBS, 100 units/ml of penicillin, 100 ug/ml of streptomycin, and hypoxanthine, aminopterin and thymidine (HAT).

The concentration of the cell suspension was adjusted to $3.3 \times 10^5$ of the spleen cells per 200 microliters of suspension. 200 microliter aliquots of suspension were then distributed to each well of a 96 well microtiter plate. After typically 20–30 such plates were prepared for each fusion, the plates were transferred to an incubator and maintained at 37° C. in 5% $CO_2$.

The cells were grown for seven days in the plates, then the growth medium was withdrawn and new medium was added. Four days after that, an enzyme linked immunosorbent assay (ELISA, below) was performed on the antibodies in the wells to determine which would bind human IgE.
2. Results Four fusion experiments with mice using the above immunization protocols were done. For these fusions, 7, 15, 36, and 15 plates of 96 wells of fusion cells were prepared, respectively. More than 98% of wells had cell growth and a well had on the average 3–5 clones of hybrids. Thus, we produced about 7,000 wells and probably 21,000–35,000 clones in the four fusions.
d) ELISA Procedure
1. Procedure The primary screening Procedure for the very large numbers of hybrids resulting from the fusion wells was ELISA with human IgE as the solid phase antigen. The polyclonal IgE purified from human sera (Ventrex) was used as the antigen.

One important and decisive strategy in our screening procedure was to screen generally high affinity antibodies from the 1,000–4,000 wells from each fusion experiment. This was done by coating very small amounts of human IgE, 50 ul of 0.1 μg/ml onto each well. Assuming all the IgE was bound to the solid phase, only 5 ng would be in each well. Because of this small amount, the possibility of screening out hybrids specific for contaminating proteins was also greatly reduced. Another very important strategic point was that only wells that show high O.D. readings were chosen for further characterization and for cloning.

In the procedure, 50 μl of 0.1 μg/ml of human IgE was added to wells of 96-well Immunlon I plates. The plates were covered and incubated for eighteen hours at 4° C. to allow the protein to bind to the plate.

The liquid contents of the plates were then emptied, and 200 ul of 0.1M $NH_4Cl$ was added to each well in order to saturate any remaining binding sites on the plates. The $NH_4Cl$ solution was left in the wells for 30 minutes at room temperature.

The $NH_4Cl$ solution was then removed and the wells were washed three times with PBS and 0.05% Tween 20. Some of the PBS/0.05% Tween 20 solution was left in the wells until the antibody suspension described below was added.

50 μl of the cell fusion supernatant from each well of the 96 well plates was added to each of the wells on the Immulon I plates, and incubated for one hour. Following incubation, the plates were rinsed three times with PBS/0.05% Tween 20 in order to remove any unbound antibody.

50 μl of the cell fusion supernatant from each well of the 96 well plates was added to each of the wells on the Immulon I plates, and incubated for one hour. Following incubation, the plates were rinsed three times with PBS/0.05% Tween 20 in order to remove any unbound antibody.

The cell fusion supernatant would contain the antibody which was produced by the various hybridomas in the 96 well plates. The antibody which was specific to human IgE would bind thereto. The amounts of antibodies bound to the solid phase were then determined by a routine procedure using horseradish peroxidase-conjugated goat-anti-mouse IgG, using 3,3′,5,5′-tetramethyl benzidine as the substrate.
2. Results From the approximate 7,000 wells screened totally, about 4,000 wells (about 60%) were positive in the ELISA. Most of these positive wells probably contained hybrids producing monoclonal antibodies for human IgE. From these approximately 4,000 wells in the ELISA, we chose 53 wells with the highest O.D. readings for cloning and further characterization.

The 53 monoclonal antibodies were checked in ELISA using wells of plates coated with human serum at various dilutions. All of them were negative in the ELISA suggesting that they did not react with human albumin, IgE, IgM, transferrin, or other major serum proteins which might have contaminated the IgE preparations used as the immunogen for mice and as the antigen in the primary screening ELISA.
d) Single Cell Cloning Cell suspensions from each of the 53 wells with the highest O.D. readings in ELISA were expanded in the wells of a twenty-four well plate, the cell suspensions were diluted to thirty, fifty and one hundred cells per milliliter. 0.1 ml of the diluted cell suspensions (containing an average of three, five and ten cells, respectively) was placed into the wells of a 96-well plate. The wells had been coated with histone.

After the cells grew up to become colonies, the cells were checked under a microscope. The cells of each colony did not move about and form colonies. The single-cell clones showing strongest reactivities in ELISA were chosen and expanded in culture.

e) Production and Purification of Monoclonal Antibodies

To produce large quantities of desired monoclonal antibodies, the following procedure was performed.

Some of the clones showing high O.D. readings in ELISA, which were grown in the wells in the twenty-four well plates, were expanded further in 100 mm tissue culture plates. The expanded culture of the selected single-cell clones were then separately injected into the peritoneal cavity of pristine treated mice, using five million cells per mouse. After seven days the ascites fluid of each mouse was collected and frozen.

The monoclonal antibodies in the ascitic fluid were purified as follows. The frozen ascitic fluid was thawed and filtered through a nylon cloth to remove viscous material. Sufficient phenylmethyl sulfonyl fluoride was added to the ascitic fluid so that there was a final concentration of 0.1 mM. 0.05 ml of 1.2M acetate buffer (pH 4.0) was added for every milliliter of ascites fluid. The final concentration of the acetate buffer was 60 mM. The pH was adjusted to 4.5.

For every milliliter of treated ascites fluid, 25 $\mu$l of caprylic acid (MW of 144.21, density of 0.91 g/ml) was added dropwise with vigorous stirring. The suspension was kept at room temperature and stirred continuously for 30 more minutes.

The suspension was then centrifuged at 15,000 g for ten minutes in order to remove the precipitate. The supernatant, which contains IgG, was neutralized by adding a volume of 1M HEPES buffer (pH 8.0) equal to one-tenth the volume of the supernatant. The IgG was then precipitated with 50% $(NH_4)_2SO_4$.

The precipitate was then dissolved in HEPES saline buffer. This solution was dialysed overnight against HEPES saline buffer in order to remove $(NH_4)_2SO_4$ from the IgG. The HEPES saline buffer was changed twice during the dialysis. After dialysis, the HEPES buffer saline contains purified dissolved IgG. The purified IgG was used in certain characterization assays.

Some monoclonal antibodies were purified from ascites or culture fluid by a dual column chromatography method. First, antibodies were chromatographed on DE-52 anion exchange resin (Whatman, Maidstone, England) using 0.05M Tris pH 8.0 with stepwise increments of NaCl from 0.01M to 0.15M. Antibody-containing fractions were identified by enzyme immunoassay, concentrated by Amicon filtration (Amicon, Danver, Mass., YM10 membrane) and purified further on a hydroxylapatite column (Bio-Gel HT; RioRad, Richmond, Calif.) using a 0.01 to 0.3M phosphate buffer (pH 7.4) step gradient. Purity was assessed by isoelectric focusing (13) and SDS-PAGE using the Pharmacia PHAST system (Pharmacia, Piscatway, N.J.) and the concentration determined by $OD_{280nm}$ (1.5 = 1 mg/ml).

EXAMPLE II: CHARACTERIZATION OF THE MONOCLONAL ANTIBODY OF THE INVENTION a) Binding to Basophils Using an Immunofluorescence Assay and a Radiobinding Assay The IgE-reactive monoclonal antibodies have been studied to determine whether they bind to basophils isolated from peripheral blood. From this second level of screening, we chose antibody to have the therapeutic value. The antibody must not bind to basophils and mast cells and cause the release of pharmacological mediators.

Intially, we chose to use immunofluorescence staining assay because basophils account for very small percentages (0.5-2%) among leukocytes. We believed that even with enriched basophil preparations, examining cells at the single cell level using immunofluorescence staining or biotin-avidin enzyme immunostaining probably gave more precise determination than radiobinding or ELISA examining the total cell populations.

1. Isolation of Basophils

Basophils were highly enriched from peripheral blood of normal, healthy individuals using density centrifugation on Percoll by adopting a procedure described by P. Raghuprasad., *J. Immunol.* 129:2128–2133 (1982). Briefly, Percoll stock solution was prepared by mixing 90 ml 90% Percoll solution with 8.96 ml 10×Hanks-balanced salt solution, 0.45 ml 1N HCl, and 1 ml 10× HEPES buffer (pH 7.6). The required densities of Percoll were prepared by using the following formula (8): Percoll density (g/ml)=(% Percoll stock solution×0.001186)+1.0041, where 0.001186 is a constant and 1.0041 the density of physiologic media. Because the density of Percoll is altered by temperature, it is prepared before the day of experiment and kept at room temperature overnight.

Heparinized blood freshly obtained from normal donors was diluted 1:1 with basic culture medium RPM1-1640 and centrifuged on a Ficoll/Hypaque cusion (density=1.070 g/ml). The mononuclear cells at the interface were removed for other uses and the whitish layer on top of the red cell pellets were recovered. These granulocytes were washed and resuspended in basic medium and then centrifuged through two carefully layered Percoll gradient of 1.072 and 1.078 g/ml at 600×g for 15 minutes. The cells recovered at the interface of the Percoll layers and below the interface of basic medium/upper Percoll layer were harvested. These cells contained 2–10% of basophils, depending on the particular individual donors.

2. Assay Procedure

50 $\mu$l of the enriched basophil suspension at a concentration of $5 \times 10^6$ cells/ml was added to each of 1.5 ml microfuge tubes containing specific antibodies. 50 ul of the supernatants from the hybridoma clones showing the greast O.D. readings in ELISA with human IgE as the antigen was then added to each tube. With some clones repetitious assays were performed. When purified antibodies were available, they were used at 20, 5 and 1 $\mu$g/ml; when ascitic fluids were available, they were used at 1:50 dilutions.

The tubes with cells and antibodies were then incubated for 30 minutes at room temperature. After incubation, the tubes were spun, the supernatant was withdrawn, and the cells were washed two times with a mixture of RPMI 1640, containing 2% fetal calf serum and 0.1% sodium azide. The tubes were then tapped to loosen the cell pellet.

10 $\mu$l of labeled antibody, goat anti-mouse IgG conjugated with fluorescein isothiocyanate (FITC), was added to each test tube at a dilution of 1 to 200. This labeled antibody will bind to any monoclonal antibodies which have attached to IgE on basophils and provide a means for identifying these monoclonal antibodies.

The tubes were again incubated for 30 minutes at room temperature. The tubes were centrifuged, and the cells were washed with the same medium as before. The cells were then resuspended in 50 ul PBS, placed onto individual slides and cover-slipped. The cells were viewed with a fluorescence microscope.

When the antibodies stained cells, one could observe that some of cells in each viewing field were stained bright. Depending on experiments the percentages of positively stained cells range about 2–10%.

3. Radiobinding Assays

Many of the steps used are similar to those for immunofluorescence staining. The leukocyte fraction containing enriched basophils is incubated with the mouse monoclonal antibody and about 10,000 cpm of $^{125}$I-goat anti-mouse IgG in the presence of 1% normal goat serum as a blocker for nonspecific binding. After 30 minutes, the incubation mixture is then overlaid on top of calf serum (100%) in a conical plastic centrifuge tube. After centrifugation to pellet the cells, the upper layer and the serum are removed. The tubes are inverted to drain the residual liquid. The tips of the cones containing the cell pellet are then cut off with a sharp razor blade. These tips are then placed in tubes and counted for $^{125}$I in a scintillation counter. The positive and negative binding is determined by comparing the amounts of bound $^{125}$I between negative control monoclonal antibody and the human IgE-specific monoclonal antibodies.

4. Results

Initially, several experiments were performed using immunofluorescence assays. More recently, tests were repeated using similar procedure employing biotin-labeled second antibody (goat anti-mouse IgG) and peroxidase-conjugated avidin. The results from the two assays indicated that the background staining varied from one antibody to another antibody. The results also indicate that sensitivities of the assays are not better than those of histamine release assays (below). The major reason for the relatively lower sensitivities in these assays was that the percentages of basophils in the blood leukocytes from the few donors selected were all very low. Individuals with relatively high basophil percentage are preferred for these immunobinding experiments. Starting with leukocytes high in basophils, one can then prepare basophil-enriched fraction, that will be suitable for these experiments.

b) Induction of Histamine Release from Blood Leukocytes

When a monoclonal antibody specific for human IgE bind to the IgE bound on basophils, it will cross-link the IgE and aggregate the underlying FcεR molecule and cause the release of histamine and other pharmacological mediators. The various human IgE-specific monoclonal antibodies were tested for ability to induce histamine release from washed human peripheral blood leukocytes.

1. Procedure

The method employed was the same as described in detail by Siraganian and Hook. The in vitro assay quantitated the percentages of total histamine in the leukocyte population that was released into the culture medium upon the incubation of inducers. The determination of histamine in the medium or cell lysates was done with an automated instrument which extracted histamine with n-butanol and reacted it with a coupling compound, o-phthaldehyde at high pH to form a fluorescent product, and measured it with fluorometer.

We performed the histamine release induction experiments, and collected media from leukocytes after the incubation with the antibodies to be tested and control antibodies, and prepared cell lysates to determine total histamine amounts.

To briefly describe the test procedure for histamine release from washed leukocytes, we adopted essentially the procedure described by Siraganian, R. P. and Hook, W. A. in *Manual of Clinical Chemistry*, ed. Rose, N. R. and Friedman, H., 2d Ed, pps 208–321, American Society of Microbiology, Washington, D.C. The blood was drawn from normal volunteers by venipuncture. In 50 ml conical tube, each 10 ml blood was mixed with 1 ml 0.1M EDTA and 2.5 ml dextrandextrose solution. (All solutions and reagents mentioned here are described in detail by Siraganian, supra.) The mixture was allowed to settle at room temperature for 60–90 minutes until a sharp interface developed between the erythrocyte and plasma layers. The plasma-leukocyte-platelet layer was drawn off and spun at 1,100 rpm for 8 minutes at 4° C. The supernatants containing the platelets were removed and 2–3 ml solution of cold PIPES A-EDTA was added and the cells were resuspended. Another 40 ml of cold PIPES A-EDTA was added and the cells were spun down. After the supernatants were removed, the cells were resuspended in 20 ml PIPES A. The cells were then spun down again and resuspended in PIPES ACM at cell density of $4 \times 10^6$/ml.

Tubes containing 0.3 ml of the washed leukocytes and tubes containing 0.3 ml of the culture medium of hybridomas were warmed up to 37° C. in 6 minutes. The tubes were mixed and incubated at 37° C. with shaking every 10 minutes. At the end of 60 minutes, the cells were spun down and the supernatants were saved. For total histamine content, 0.3 ml of the washed leukocytes were mixed with 6% perchloric acid.

2. Results

Recognizing the unreliability in the nature of the histamine release among the blood donors available to us, we contracted the histamine assay to an outside laboratory which routinely performs histamine release assays. Dr. Donald MacGlashan's laboratory in the Department of Clinical Chemistry in Johns Hopkins University determined the abilities of most of our human IgE-specific monoclonal antibodies for abilities to induce histamine release from basophils. The key results relating to those monoclonal antibodies which did not induce histamine release were then confirmed at Dr. Reuben Siraganian's laboratory in National Insitute of Health. Both of these laboratories have established a stable population of high histamine releasers from screening large number of blood donors. The results of the extensive studies using leukocytes from seven donors including at least four high releasers performed by Dr. MacGlashan are summarized in Table I. The antibodies were diluted 100, 10,000, or 1,000,000 folds from ascitic fluids or purified antibodies (1 to 5 mg/ml). The histamine release data were from one representative "superreleaser". The results showed that among the 41 monoclonal antibodies, 12 did not induce histamine release.

TABLE I

Reactivity With IgE-Bearing Cells and Ability to Induce Histamine Release by Basophils of Mouse Monoclonal Antibodies Specific for Human IgE

| Monoclonal Antibodies | Binding to SK007 Cell Flow Cytometry | Histamine Release Antibody Dilution $1/10^2$ $1/10^4$ $1/10^6$ (% of Total Release) | | |
|---|---|---|---|---|
| Group I | | | | |
| E101-1 ($r_{2a}$, k) | + | 0 | 0 | 0 |
| E8-5-3 ($r_{2b}$, k) | + | 0 | 0 | 0 |
| E10-21-15 ($r_1$, k) | + | 0 | 0 | 0 |

TABLE I-continued

Reactivity With IgE-Bearing Cells and Ability to Induce Histamine Release by Basophils of Mouse Monoclonal Antibodies Specific for Human IgE

| Monoclonal Antibodies | Binding to SK007 Cell Flow Cytometry | Histamine Release Antibody Dilution (% of Total Release) | | |
|---|---|---|---|---|
| | | $1/10^2$ | $1/10^4$ | $1/10^6$ |
| E10-8-120 ($r_1$, k) | + | 0 | 0 | 0 |
| E10-12-55 ($r_{2a}$, k) | + | 0 | 0 | 0 |
| E11-4-70 ($r_{2b}$) | + | 0 | 0 | 0 |
| Group II | | | | |
| E10-55-31 ($r_1$, k) | − | 0 | 0 | 0 |
| E8-13-1 ($r_1$, k) | − | 0 | 0 | 0 |
| E8-32-9 ($r_1$, k) | − | 0 | 0 | 0 |
| E357-4 ($r_1$, k) | − | 0 | 0 | 0 |
| E8-37-4 ($r_1$, k) | − | 0 | 0 | 0 |
| E8-4-17 ($r_1$, k) | − | 0 | 0 | 0 |
| Group III | | | | |
| E69-2 ($r_1$, k) | + | 44 | 13 | 0 |
| E10-100-9 ($r_{2a}$, k) | + | 68 | 45 | 0 |
| E10-41-16 ($r_{2a}$) | + | 95 | 91 | 91 |
| E10-95-3 ($r_{2b}$, k) | + | 65 | 68 | 3 |
| E10-68-10 ($r_1$, k) | + | 56 | 42 | 2 |
| E10-10-3 ($r_1$, k) | + | 85 | 78 | 2 |
| E10-5-83 ($r_1$, k) | + | 82 | 80 | 6 |
| E10-24-28 ($r_{2b}$, k) | + | 79 | 89 | 5 |
| E10-27-5 ($r_{2b}$, k) | + | 68 | 90 | 9 |
| E10-22-84 ($r_{2a}$, k) | + | 77 | 84 | 15 |
| E10-74-28 ($r_1$, k) | + | 60 | 65 | 3 |
| E10-1-88 ($r_1$, k) | + | 72 | 55 | 2 |
| E10-3-14-25 ($r_1$, k) | + | 68 | 58 | 3 |
| E10-7-19 ($r_1$, k) | + | 38 | 26 | 6 |
| E10-18-3 ($r_1$, k) | + | 33 | 26 | 0 |
| E10-40-62 ($r_{2b}$, k) | + | 37 | 24 | 9 |
| E10-19-12 ($r_1$, k) | + | 28 | 37 | 36 |
| E10-52-38 ($r_1$, k) | + | 57 | 64 | 14 |
| E10-54-26 ($r_1$, k) | + | 34 | 17 | 2 |
| E235-6 ($r_1$, k) | + | 52 | 25 | 12 |
| E10-14-52 ($r_1$, k) | + | 52 | 24 | 0 |
| E10-71-47 ($r_1$, k) | + | 30 | 16 | 0 |
| E10-25-44 ($r_{2b}$, k) | + | 31 | 26 | 0 |
| E10-61-6 ($r_1$, k) | + | 81 | 78 | 70 |
| E10-33-22 ($r_{2a}$) | + | 77 | 74 | 16 |
| E608-10 ($r_1$) | + | 81 | 84 | 86 |
| E688-13 ($r_1$) | + | 86 | 91 | 90 |
| E10-80-4 ($r_{2b}$) | + | 85 | 92 | 90 |
| E545-4 ($r_1$, k) | + | 24 | 3 | 0 | c) Binding of Monoclonal Antibodies to IgE-secreting Myeloma Cells

Some myeloma cells (which are tumor cells derived from immunoglobulin-secreting plasma cells) are known to express low levels of immunoglobulins on their surface, compared to those on the surface of resting B cells. IgE molecules are bound to the surfaces of basophils (or mast cells) and B cells by two different mechanisms. IgE binds to basophils and mast cells via the interaction of FcεR molecules on these cells and a certain site on the Fc of IgE. IgE are synthesized by B cells or plasma cells and are transported to the cell surface and retained on the surface by an extra constant heavy chain segment. This anchoring segment is found only in membrane-bound immunoglobulins and not in secreted forms of immunoglobulins. The differential binding of a monoclonal antibody to IgE on basophils and on B cells is a fundamental basis for the application of the antibodies for therapy of allergy.

Since IgE-bearing B cells and plasma cells are very few in the mononuclear leukocyte fraction and since the topographical and structural characteristics of membrane-bound IgE molecules are most likely the same on plasma cells, B cells or IgE-secreting myeloma cells, we have chosen to study the binding of monoclonal antibodies to IgE myeloma SK007 (from American Type Culture Collection) cells. The interaction of the monoclonal antibodies can also be examined with normal IgE-bearing B cells and plasma cells.

1. Procedure

Human SKO-007, CCL-156 and CCL-159 cells, expressing surface-bound human IgE-lambda, IgM-lambda and IgG1-kappa, respectively, were maintained in RPMI medium 1640 supplemented with 5% fetal bovine serum and 2 mM glutamine from GIBCO and 1% antibiotic-antimycotic solution. Peripheral blood mononuclear cells obtained by venipuncture of healthy donors were prepared by Ficoll-paque (Pharmacia, Piscataway, N.J.) density gradient centrifugation. Binding of monoclonal antibodies to cell surfaces was assessed using two types of assays: binding of antibodies to live cells followed by indirect fluorescent flow cytometric analysis and an enzyme-linked antibody assay with the cells attached to microtiter plates.

Binding of antibodies to live cells was performed by pelleting the cells by centrifugation at 300×g for 5 min. washing maintenance media from the cells with PBS-BSA and resuspending the cells at 20×10⁶ in PBS-B. Fifty μl of cell suspension was mixed with 50 μl of antibody at twice the stated concentrations (1–10 μg/ml) in PBS-B and kept on ice. After a 30 min incubation, 2 ml of ice cold PBS-B was added to each tube, and the cells were collected by centrifugation at 300×g for 5 min at 5° C. Supernatant was decanted, cell pellets resuspended by vortexing and cells washed once with an additional 2 ml of PBS-B. After collecting the cells by centrifugation, 20 ul of affinity purified goat F(ab')₂ anti-mouse IgG (H+L) (Boehringer Mannheim, Lot 52934, code 60529) diluted 1:20 in PBS-B was added to each tube. The tubes were incubated 20 min on ice and washed with PBS-B as above. Finally, cell pellets were resuspended in 0.5 ml of 1% paraformaldehyde (Polysciences, Inc., Warrington, Pa.) in PBS. Cells were analyzed using a EPICS Profile (Coulter, Hialeah, Fla.) equipped with a 5W argon laser running at 488 nm, 0.6W at Cytology Technology, Inc. (Houston, Tex.). Fluorescence intensity was collected with a built-in logarithmic amplifier after gating on the combination of forward light scatter and perpendicular light scatter to discriminate viable cells.

The cell-bound enzyme-linked antibody assay was performed by binding MAbs to glutaraldehyde-fixed cells according to the method of Kennett, R. H. in Monoclonal Antibodies eds. Kennett, R. H. et al., pp. 376, Plenum Press, New York (1980). Poly-L-lysine (100 μl/well, 10 μg/ml in PBS) was added to flat bottomed microtiter plates (Falcon #3072, Becton Dickinson Labware, Oxnard, Calif.). This solution was flicked out of the wells after 30 min at 22° C. and 50 ul of cells at 2.5×10⁶ cells/ml of calcium and magnesium-free Dulbecco-modified PBS (GIBCO) was added to each well. Cells were deposited on the bottom of the wells by centrifugation at 300×g for 5 min and cells were fixed at 22° C. for 10 min by adding 50 ul of glutaraldehyde diluted to 0.25% in ice-cold PBS. Non-specific binding sites were blocked by sequential incubation of 0.1M glycine-0.1% BSA in PBS (200 ul/well) followed by Blotto [5% non-fat dry milk (Carnation, LA, Calif.) in PBS with 1 g/L of thimerosal]. Blocking solutions were removed by gentle flicking of the plate. Cells were exposed to 50 ul/well of control or test monoclonal antibody in Blotto for 1 hr at 37° C. Unbound antibody was removed by flicking the plate and washing 6 times with 200 ul/well of PBS using a Transtar 96 pipetting device (Costar, Cambridge, Mass.). Subsequently, the cells were incubated with 50 ul biotin-labeled affinity-purified goat anti-mouse IgG(KPL, Gaithersburg, Md.) at 0.5 ug/ml in Blotto for 1 hr at 37° C. All wells were washed as above and horseradish peroxidase-streptavidin was added at 0.5 ug/ml in Blotto for 1 hr at 37° C. Unbound conjugate was removed by washing as above and 100 ul of TMB substrate was added. The plates were kept in the dark for 30 min at 22° C. and the reaction was stopped with the addition of 50 ul/well of 4N $H_2SO_4$. Optical denisty at 450 nm was measured using a Biotek microtiter plate reader.

2. Results

Among the 41 monoclonal antibodies tested with flow cytometric analyses, 35 were shown to stain SK007 cells. All of the 29 monoclonal antibodies which induced histamine release from basophils, stained. Among the 12 monoclonal antibodies, which did not induce histamine release, 6 stained and 6 did not stain SK007 cells (Table I). The results with enzyme immunostaining were the same as those with flow cytometric assays. Thus, in the group of monoclonal antibodies that have been analyzed, six fit the criteria that they do not bind to basophils and induce histamine release and that they bind to IgE-producing B cells. As discussed earlier, Siraganian and his colleagues (*Fed. Proc.* 46:1346, (1987) developed two mouse monoclonal antibodies (E14C5IB1 and E11AC3IIC) against human IgE that could inhibit binding of IgE to basophils. We obtained these two antibodies from Dr. Siraganian and showed that they bind to SK007 cells and do not induce histamine release from basophils.

d) Determining the Binding Affinity with Human IgE

1. Principle and Procedure

It is well known that the sensitivity of immunoassays depends on the affinities of the antibodies for the substances to be measured. In the cases of solid phase sandwich immunoassays using two monoclonal antibodies, one as the solid-phase adsorbent and one as the tracer, both of the affinities of the two monoclonal antibodies for the antigen are important. The influence of antibody affinity on the performance of different antibody assays and the use of immunoassays for calculating antibody affinity have been systematically studied. Nimmo et al. *J. Immunol. Met.* 72:177–187 (1984); Muller *J. Immunol. Met.* 34:345–352 (1980).

For determining the affinity of a monoclonal antibody for an antigen, one can coat the antigen on the solid phase of an immunoassay, for example, the microtiter wells of a 96-well ELISA plate. The affinity of a monoclonal antibody relative to that of a reference monoclonal antibody for the same antigen on the solid phase can be determined by comparing the two monoclonal antibodies in the immunoassay. The affinity or the association constant of the reference monoclonal antibody has been determined by a certain other method or a similar method. The O.D. readout of the monoclonal antibody which affinity is to be determined in comparison to that of the reference monoclonal antibody will indicate whether the affinity of that monoclonal antibody is greater or lower than that of the reference monoclonal antibody.

When a reference monoclonal antibody is not available, the analysis can be made against a reference monoclonal antibody specific for a different antigen. By coating same molar amount antigen on the solid phase and applying all other assay conditions and parameters identical, the relative affinity of the two monoclonal antibodies can be determined from the O.D. readouts.

In our determination of the affinities of the several human IgE-specific monoclonal antibodies that bind to SK007 cells but do not induce histamine release from basophils, we compared the binding of various monoclonal antibodies to human IgE with that of a monoclonal antibody to human $\beta$-HCG, which affinity has been determined to be $1 \times 10^{11}$ liter/mole. In our assays, we coated 50 ul of 0.1 ug/ml of $\beta$-HCG or human IgE on the wells of an ELISA plate and titrated the anti-HCG monoclonal antibody and the various monoclonal antibodies against the respective antigens on the solid phase. The procedure was in effect the same as described in the ELISA procedure in Example I. By using horseradish peroxidase-conjugated goat-anti-mouse IgG and the enzyme substrate, the titration curves were determined.

The affinity of monoclonal antibodies of interest can also be determined by $^{125}$I-labeled human IgE. The solutions of the antibodies and $^{125}$I-IgE of known concentrations are mixed and the mixture is allowed sufficient time (24 hours) for the binding to reach to equilibrium. The immune complexes are then swiftly removed by affinity adsorption using excess Sepharose 4B conjugated with goat-anti-mouse IgG. The free $^{125}$IgE is washed off swiftly. From the proportions of free $^{125}$I-IgE and bound $^{125}$I-IgE, the association constant, Ka, of the monoclonal antibody can be calculated. This method is especially suitable for antibodies of high affinity.

2. Results

The six monoclonal antibodies that do not induce histamine release from basophils and that bind to SK007 cells have been determined to have association constant, Ka, in the range of $3 \times 10^8$ to $5 \times 10^9$ liter/mole.

Equivalents

Those skilled in the art will recognize, or be able to ascertain using no more than routine experimentation, many equivalents to the specific embodiments of the inventions described herein. Such equivalents are intended to be encompassed by the following.

I claim:

1. A rodent/human antibody having an antigen binding region of rodent origin and an IgG1 or IgG3 constant region of human origin which binds to secreted IgE and to the membrane-bound form of IGE expressed on the surface of IGE-bearing B lymphocytes but not to IgE which is bound to the FcɛRI on basophils basophils.

2. An antibody of claim 1, wherein the rodent is a mouse.

* * * * *

UNITED STATES PATENT AND TRADEMARK OFFICE
CERTIFICATE OF CORRECTION

PATENT NO. : 5,428,133  Page 1 of 2
DATED : June 27, 1995
INVENTOR(S) : Chang

It is certified that error appears in the above-indentified patent and that said Letters Patent is hereby corrected as shown below:

On the title page, Item [75] inventor: "Tse-wen Chang" should read --Tse Wen Chang--.

On the title page, item [54] and column 1 lines 2 thru 6 should read:

Second line, decapitalize "g" in "IgE";

Third line, decapitalize "g" in "IgE";

Fourth line, decapitalize "g" in "IgE";

Fifth line, decapitalize "g" in "IgE"; change "NOTTO" to -- NOT TO--;

Sixth line, decapitalize "g" in "IgE"; decapitalize "c" in "Fc".

Col. 1, line 45, put a space after "(Fcε)".

Col. 2, line 34, change "of" to -- or --.

Col. 2, line 65, insert "of" after "forms".

Col. 7, line 15, change "Antiidiotypic" to -- Anti-idiotypic --.

Col. 13, line 26, change "suspension" to -- suspensions --.

Col. 13, line 56, decapitalize the "P" in "Procedures".

UNITED STATES PATENT AND TRADEMARK OFFICE
CERTIFICATE OF CORRECTION

PATENT NO. : 5,428,133
DATED : June 27, 1995
INVENTOR(S) : Chang

It is certified that error appears in the above-indentified patent and that said Letters Patent is hereby corrected as shown below:

Col. 20, line 34, insert "for" before -- 20 --.

Col. 13, line 39, eliminate the period after "C".

Col. 5, line 59, change "membrane-lyric" to -- membrane-lytic --.

Col. 8, line 4, change "lymphold" to -- lymphoid --.

Claim 1 (Col. 22, line 55) change "membrance-bound" to -- membrane-bound --, and decapitalize the "g" in "IgE".

Col. 22, line 56, decapitalize the "g" in "IgE".

Col. 22, line 57, delete the second occurrence of "basophils".

Signed and Sealed this

Seventeenth Day of October, 1995

Attest:

BRUCE LEHMAN

*Attesting Officer*          *Commissioner of Patents and Trademarks*